United States Patent [19]
Morejohn et al.

[11] Patent Number: 6,086,557
[45] Date of Patent: Jul. 11, 2000

[54] BIFURCATED VENOUS CANNULA

[75] Inventors: Dwight P. Morejohn, Davis; Michael V. Morejohn, San Jose, both of Calif.

[73] Assignee: Cardiothoracic Systems, Inc., Cupertino, Calif.

[21] Appl. No.: 09/165,162

[22] Filed: Oct. 1, 1998

[51] Int. Cl.⁷ ..................................................... A61N 5/00
[52] U.S. Cl. ........................... 604/96; 604/101; 604/532; 604/500; 604/509; 606/192; 606/194
[58] Field of Search .............................. 604/96, 101, 523, 604/532, 534, 500, 509; 606/192, 194

[56] References Cited

U.S. PATENT DOCUMENTS

| | | | |
|---|---|---|---|
| 4,309,994 | 1/1982 | Grunwald | 128/214 |
| 5,562,606 | 10/1996 | Huybregts | 604/8 |

*Primary Examiner*—John D. Yasko
*Attorney, Agent, or Firm*—Lyon & Lyon LLP

[57] ABSTRACT

A cannula for draining blood from a patient's heart during cardiac surgery including a main body and a pair of branches extending distally therefrom. The branches are biased to extend away from one another by pre-shaped stiffening elements, and have "D" shaped cross-sections defining flat surfaces oriented generally towards one another. The branches may be constrained in a retracted position, the flat surfaces abutting one another, and the resulting profile forming a substantially continuous extension of the main body. The branches have distal tips including drainage holes and occlusion balloons, and elbow portions including accordion-like ridges for preventing kinking. Grooves in the flat surfaces define a secondary lumen in the retracted position through which a cardioplegia delivery or an imaging device may be advanced. The cannula is directed into a trocar to constrain the branches in the retracted position, and the trocar is inserted into the right atrium. The trocar is withdrawn to deploy the branches, which automatically extend away from one another, assuming a tripartite configuration wherein the branches extend substantially transversely from the main body, and enter the superior and inferior vena cavae. The occlusion balloons are inflated to isolate the vena cavae and blood is drained therefrom for delivery to a pump-oxygenator. A cardioplegia delivery device is advanced through the secondary lumen into the coronary sinus, an occlusion balloon on a distal tip of the device is inflated to isolate the coronary sinus, and retrograde delivery of cardioplegia is achieved.

27 Claims, 5 Drawing Sheets

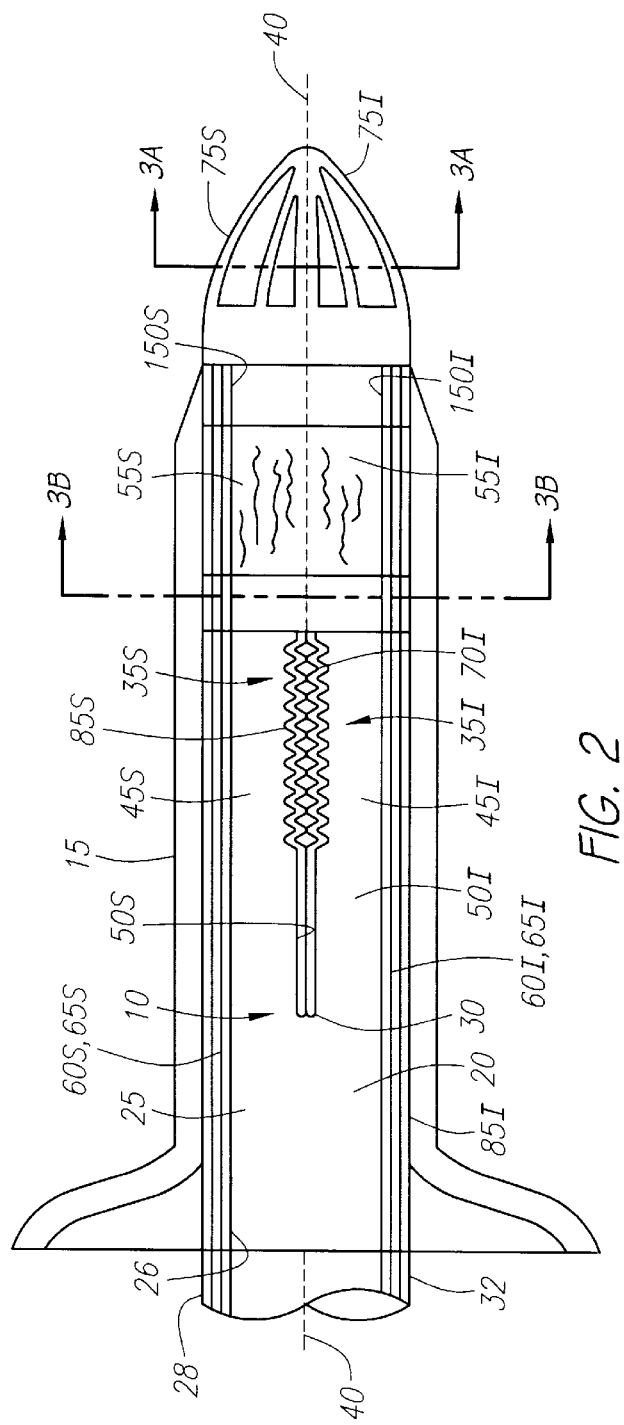
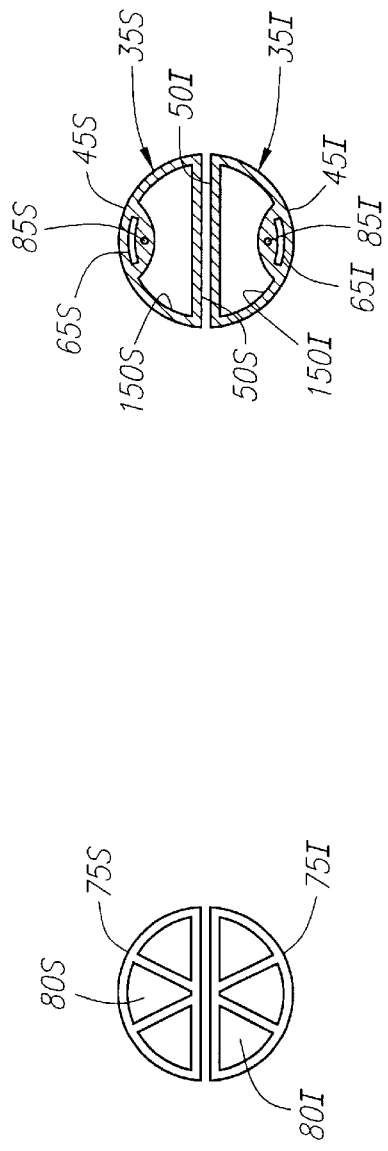
FIG. 2
FIG. 3A
FIG. 3B

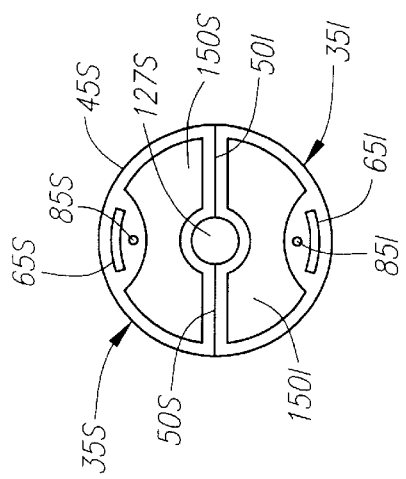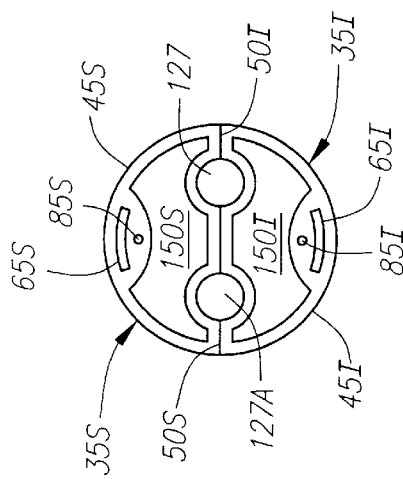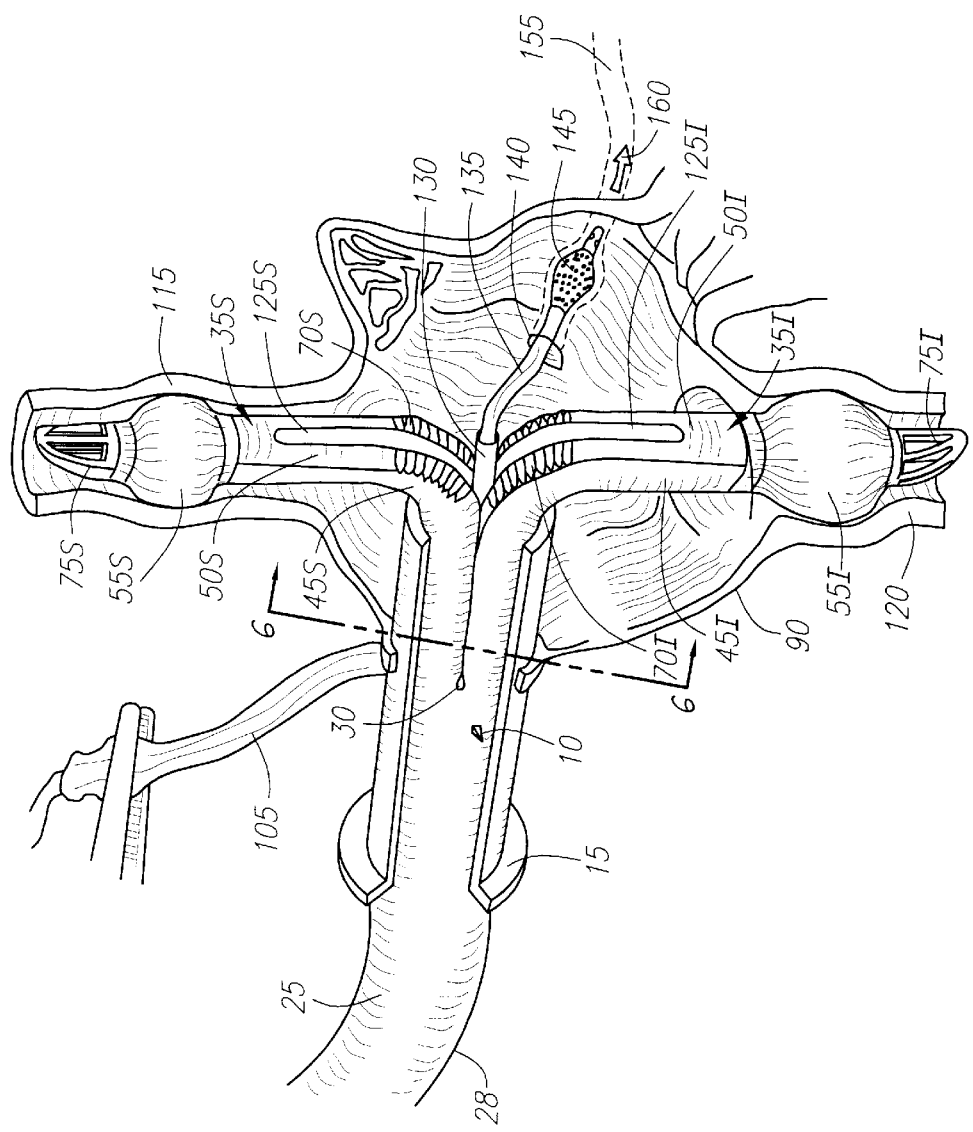

BIFURCATED VENOUS CANNULA

FIELD OF THE INVENTION

The present invention relates generally to surgical instruments, and more specifically to cannulae for use during heart surgery.

BACKGROUND OF THE INVENTION

The essential goals of cardiopulmonary bypass (CPB) are to provide life support functions, a motionless and decompressed heart, and a bloodless field of view to facilitate cardiac surgery. CPB requires the use of cannulae to divert de-oxygenated blood from its normal circulatory path, through a heart-lung machine (i.e., a pump-oxygenator), and return oxygenated blood to the patient. This generally includes using both venous and arterial cannulae, and flushing the heart's coronary system with cardioplegia to arrest the heart. In a basic CPB system, oxygen-poor blood is drained by gravity or is siphoned from the patient's venous circulation and is transported to the heart-lung machine where carbon dioxide is removed from the blood and oxygen is added. The oxygenated blood is then returned or perfused into the patient's arterial circulation for distribution throughout the patient's entire body. This process requires a venous drainage cannula (or cannulae) to be placed into the right side of the heart (e.g. the right atrium), directly into the major veins (e.g. the superior vena cava (SVC) and/or the inferior vena cava (IVC)), or through peripheral vein access sites, to drain de-oxygenated blood from the patient and then deliver the blood to the heart-lung machine. Similarly, an arterial or aortic perfusion cannula is typically placed in the aorta or other large peripheral artery, such as the common femoral artery, to return or perfuse oxygenated blood to the patient. The patient's heart and lungs can thus effectively be bypassed, allowing surgeons to operate on a bloodless heart.

The venous cannula or cannulae are inserted usually directly through an incision in the right atrium or into the SVC and/or IVC for connection to the drainage side of the pump-oxygenator. Once the cannulae are in place and the connections are made to the heart-lung machine, CPB is instituted by allowing de-oxygenated blood returning to the right side of the heart to be diverted through the venous drainage cannula(e) and into the pump oxygenator where it is oxygenated and temperature-adjusted. From there, the blood is pumped into the patient's arterial system via the arterial or aortic perfusion cannula to provide oxygen-rich blood to the patient's body and brain.

If it is desired to drain or siphon blood from both the SVC and the IVC, two cannulae are typically used—one for each vena cava. This requires more work due to multiple incisions, multiple sutures, multiple connections to the heart-lung machine, etc., and may also obstruct the surgeon's view and the surgeon's access. To overcome these and other problems, it has been suggested that a single cannula be used, as shown, example, in U.S. Pat. No. 5,562,606 issued to Marinus, and U.S. Pat. No. 4,309,994 issued to Grunwald, both of which are expressly incorporated herein by reference. Marinus describes a cannula that is inserted through one of the vena cavae and extends through the right atrium into the other vena cava, wherein the cannula is provided with a cooling structure to help cool the right atrium. Grunwald describes a cannula that branches in two directions to allow drainage of both vena cavae, but requires the use of an obturator inserted therein to force the diverging branches together (e.g., for insertion or removal of the cannula through a trocar port). In addition, because the combined transverse cross-sectional areas of the two branches in Grunwald is less than the transverse cross-sectional area of the main cannula body from which the branches diverge, Grunwald appears to make inefficient use of the available drainage volume of the branches. Similarly, the drainage in Grunwald may be restricted due to possible kinks in the branches at the points where they diverge (referred to in Grunwald as the crotch).

SUMMARY OF THE INVENTION

The present invention relates to improved devices and methods for draining or siphoning blood from both vena cavae, typically during CPB. In a preferred embodiment, a device of the present invention comprises a single drainage cannula with a common primary body having a common primary lumen that leads to a junction or bifurcation point where the cannula is bifurcated into two branches. Each branch has its own primary branch body and corresponding primary branch lumen, and terminates at its own distal tip where blood from the SVC and IVC, respectively, may be drained or siphoned from a patient's circulatory system. The two branches diverge from each other during deployment, e.g., the branches are preferably biased to extend substantially transversely relative to a common longitudinal central axis of the common primary body.

In a preferred embodiment of the present invention, the two branches are each substantially "D-shaped" in transverse cross-section, each having an arced surface and a flat surface. Thus, when the branches are constrained in a fully retracted position prior to deployment, their flat surfaces face inwardly toward each other, preferably abutting one another, and arced surfaces facing outwardly away from each other. Preferably, the profile of the branches is such that in the retracted position, they form a substantially continuous extension of the non-bifurcated portion of the cannula. Constraining the cannula in the fully retracted position typically requires a securing wall, such as a trocar sleeve, to be placed around the cannula, as the branches in a preferred embodiment,will naturally diverge due to pre-shaped stiffening elements or aligners, which may, for example, be comprised of a shape-memory material, such as Nitinol. The cannula in a fully retracted position thus has a substantially uniform transverse cross-section, and can therefore be inserted through a trocar sleeve having a similar inner cross-section. As the cannula is deployed, thus extending the branches beyond the securing trocar sleeve, the branches automatically separate from each other to assume a substantially "tripartite" configuration with respect to the common primary body. In the tripartite configuration, the branches preferably extend away from one another substantially transversely with respect to the central longitudinal axis of the common primary body. In one preferred form, the tripartite configuration results in a generally "Y" shaped cannula with the branches having angles of about +45° and about −45°, respectively, and in another preferred form, the tripartite configuration results in a generally "T" shaped cannula with branch angles of about +90° and about −90°, respectively, with respect to the central longitudinal axis of the common primary body. Thus, in the tripartite configuration, the cannula may define an angle between the branches of between about 90° and about 180°.

Secondary lumens may also exist for a variety of other purposes. There may be secondary lumens for securing the pre-shaped stiffening elements in or on the branches to provide a naturally diverging bifurcation, or alternatively the stiffening elements may be embedded directly into the wall of the branches. There may also be secondary lumens for inflating occlusion members, such as balloons, near the distal tips of the branches, or for inserting an imaging device or a cardioplegia delivery device through the cannula. A particular secondary lumen may be dedicated to a single purpose, or it may be available for multiple functions at differing times. Thus, associated with the cannula there may be occlusion balloons, a cardioplegia delivery mechanism, and/or a viewing device, such as an endoscope or ultrasound imaging device.

The branches may also have accordion-like ridges on outer portions thereof, i.e., at rounded elbow portions that bend near the junction. This may help prevent kinks in the branches which might obstruct the flow of blood.

In another aspect of the present invention, a method is provided for introducing a bicaval venous cannula into the right atrium of a patient's heart for draining blood during cardiac surgery. A bifurcated cannula having a main body and first and second branches extending distally from the main body may be provided, such as the cannula described above. The branches may be inserted into the right atrium in a retracted condition wherein the first and second branches abut one another to assume a profile substantially similar in cross-section to the profile of the main body. The first and second branches may then be directed away from one another until the branches assume a tripartite configuration, such as a generally "Y" or "T" shape, and the first and second branches enter the superior and inferior vena cavae, respectively.

In a preferred form, the branches are biased towards the tripartite configuration, but are constrained in the retracted condition during insertion into the right atrium. For example, the branches may include pre-shaped stiffening elements for biasing the branches towards the tripartite configuration. The stiffening elements may be attached to the branches prior to insertion into the right atrium, and may be removed from the branches after the first and second branches are positioned within the superior and inferior vena cavae, respectively. The stiffening elements may also be inserted into supplemental lumens in the branches to attach the pre-shaped stiffening elements to the branches and to bias the branches towards the tripartite configuration, or alternatively, the stiffening elements may be substantially permanently attached to the branches.

The bifurcated cannula may be directed into a trocar, preferably having an inner cross-section similar to the profile of the main body, to constrain the branches in the retracted condition. The trocar, with the branches constrained in the retracted condition therein, may be inserted through an incision in the wall of the heart into the right atrium. The trocar may then be withdrawn proximally while substantially retaining the branches in the right atrium, thereby automatically directing the branches away from one another as the branches are deployed from the trocar. Once the branches are properly positioned in the vena cavae, occlusion members, such as balloons, on the distal tips of the first and second branches may be expanded to substantially engage the walls of the respective vena cava, i.e., to substantially isolate the superior and inferior vena cavae, respectively, from the right atrium.

In another preferred form, the first and second branches include surfaces adapted to abut one another when the branches are in the retracted condition. The surfaces may include grooves extending axially along the surface, the grooves together at least partially defining a lumen when the branches are in the retracted condition, the lumen extending proximally into the main body. For example, a distal portion of a cardioplegia catheter and/or cannula may be advanced through the lumen into the right atrium, and further into the coronary sinus, and cardioplegia may be delivered into the coronary sinus through the cardioplegia catheter. In addition, an occlusion member on the distal portion of the cardioplegia catheter may be expanded to substantially isolate the coronary sinus from the right atrium prior to delivering cardioplegia into the coronary sinus. Alternatively, an imaging device may be advanced through the lumen, or through a separate lumen, to view the right atrium prior to directing the first and second branches away from one another, or alternatively during other stages of a procedure.

BRIEF DESCRIPTION OF THE DRAWINGS

FIG. 2 is a cross-section of a cannula according to a preferred embodiment of the present invention, showing the cannula in a fully retracted position secured within a trocar sleeve.

FIGS. 3A and 3B are cross-sections along lines 3A—3A and 3B—3B, respectively, of FIG. 2, showing the orientation of the tips of the branches with respect to each other when the cannula is in a fully retracted position and the lumens within the branches, respectively.

FIG. 5 is a cut-out view of a heart with an alternative embodiment of a cannula of the present invention deployed therein, showing a cardioplegia delivery device.

FIGS. 6A and 6B are cross-sections along line 6—6 of FIG. 5, showing the various lumens of the cannula in an embodiment having a cardioplegia delivery lumen.

DETAILED DESCRIPTION

Figure 1:
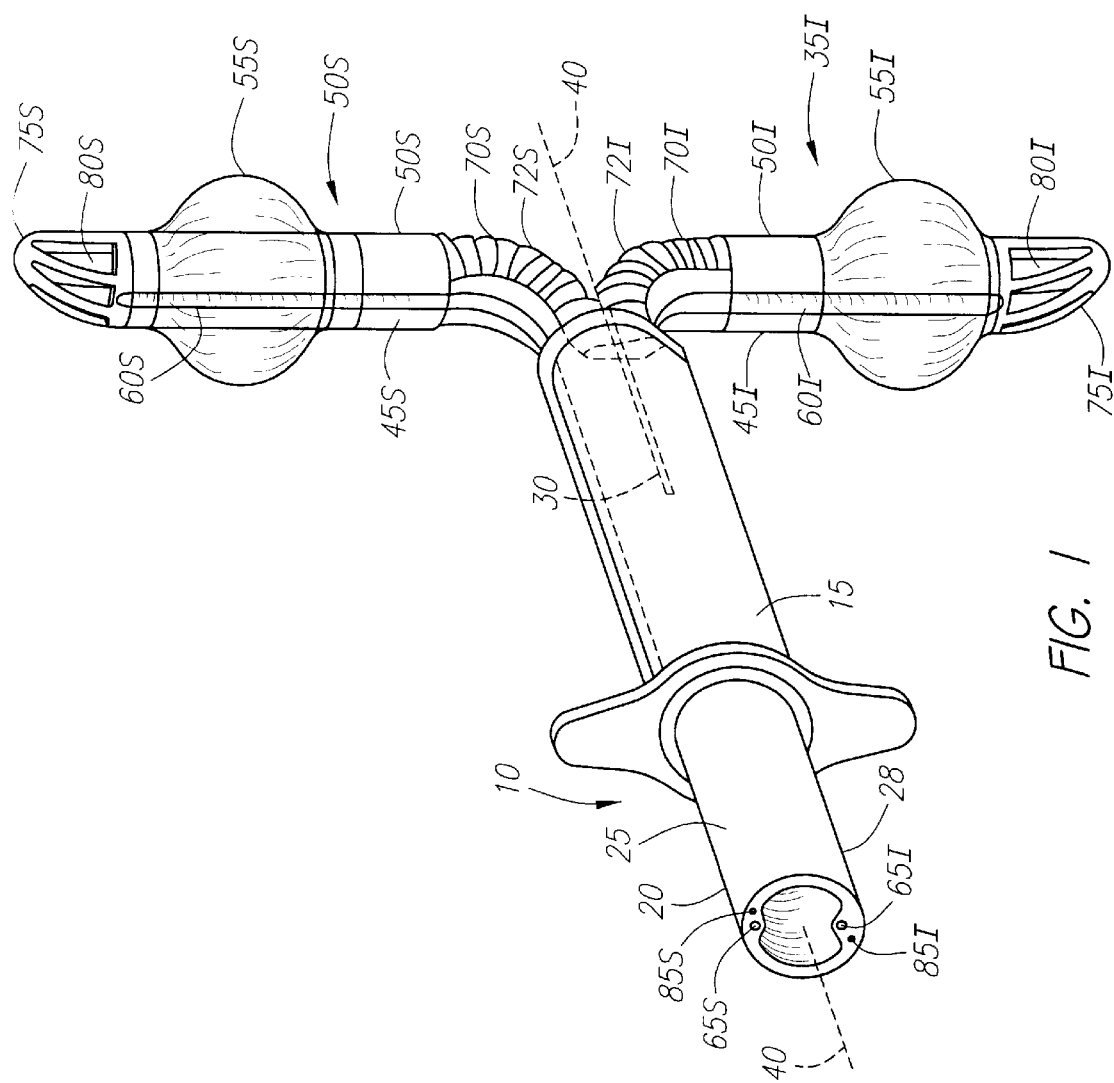
FIG. 1 is a perspective view of a cannula according to a preferred embodiment of the present invention, showing the cannula being deployed through a trocar sleeve and bifurcating into a "T" configuration.

FIG. 1 shows a cannula 10 according to a preferred embodiment of the present invention, being deployed through a trocar sleeve 15. The cannula 10 may be injection molded and formed of a flexible material such as polyvinyl or silicone. At its proximal end 20, the cannula 10 may be connected to the venous drainage of a heart-lung machine (not shown). The cannula 10 has a primary common body 25, that splits at a junction or bifurcation point 30 into two branches 35S (the SVC branch) and 35I (the IVC branch). (Various features of the cannula 10 will be labeled with an "S" or an "I" after the reference numerals, to correspond to the respective branches 35S or 35I respectively. This is merely for a matter of convenience when referring to the drawings, but unless otherwise noted the branches 35S and 35I are preferably mirror images of each other with respect to the central longitudinal axis 40 of the cannula 10. However, when referring generically to either branch 35S or 35I, or to a feature or cooperating element of either branch 35S or 35I, the trailing "S" or "I" will be omitted.)

The branches 35 are preferably "D-shaped" in transverse cross-section, as best seen in FIG. 3B. Each branch 35 thus has an arced surface 45 and a flat surface 50.

As shown in FIG. 2, when the branches 35 are in a fully retracted position, the flat surfaces 50 face inwardly toward each other, preferably abutting one another, and arced surfaces 45 facing outwardly away from each other such that with expandable members 55 deflated, the branches 35 preferably form a substantially continuous extension of the primary common body 25. The transverse cross-section of the cannula 10 in a fully retracted position thus has a substantially uniform, preferably circular, perimeter, whether the cross-section is taken from the primary common body 25 or from the combined branches 35S and 35I. The cannula 10 can therefore be inserted through a trocar sleeve 15 having a similar inner cross-section. In this manner, the maximum combined volume of the branch lumens 150 can be achieved because there is no unused space between the branches 35 as they pass through the trocar sleeve 15.

When referring to two-dimensional figures in this application, "D-shaped" shall mean not only literally D-shaped, but shall include any two-dimensional, closed geometric shape having an arced portion connected by a straight portion to create a closed figure. For example, a semi-circle with a diameter connecting the two endpoints of the arc is D-shaped. Similarly, U's, C's, portions of an oval, or other elliptical shapes, with two points on an arc connected by a substantially straight line, are also D-shaped.

Returning to FIG. 1, as the cannula 10 is deployed, thus extending beyond its securing trocar sleeve 15, the flat surfaces 50 of branches 35 may be directed apart from each other, preferably automatically separating to seek a "tripartite" configuration, i.e., wherein the branches 35 extend away from one another substantially transversely, with respect to the central longitudinal axis 40 of the primary common body 25. In the tripartite, configuration, the divergence of the branches 35 may range from about +45° and about −45°, respectively, (a Y-shaped cannula) to about +90° and about −90°, respectively, (a T-shaped cannula, as seen in FIG. 1) with respect to the central longitudinal axis 40 of the cannula 10. The branches 35 diverge or are outwardly biased and conform substantially to the anatomy of the patient's vena cavae, preferably to a predetermined angle of about 90° each with respect to the longitudinal axis 40. Preferably, the branches 35 are biased to extend substantially transversely with respect to the central longitudinal axis 40 due to pre-shaped stiffening elements, such as Nitinol or other shape-memory-alloy aligners 60, located in or on the branches 35. The aligners 60 are preferably inserted through secondary lumens 65 and tightly fitted in position within or on the branches 35. Alternatively, the stiffening elements may be embedded substantially permanently into the walls of the branches 35. The aligner 60 may be a cylindrical wire (see FIG. 1), a flat band (see FIG. 6A lumens 65), or other configuration.

Accordion-like ridges 70 are preferably provided on the branches 35, at least at the outer portions thereof that are pre-shaped to be bent during deployment, i.e., at rounded elbow portions 72. This may help prevent kinks in the branches 35 which might obstruct the flow of blood through the branch lumens 150. The ridges 70 are preferably on the outside surfaces of the branches 35 so as not to interfere with the flow of blood through the branch lumens 150 and to allow expansion of lumen material as it is opened or stretched.

Each branch 35 terminates at a distal tip 75 having a shape adapted to facilitate introduction into the right atrium. Each distal tip 75 has drainage holes 80 therethrough for draining or siphoning blood out of the patient and into the heart-lung machine. As best seen in FIG. 3A, the drainage holes 80 are preferably wedge-shaped to correspond to the curvature of the tips 75. The wedge-shaped holes 80 may minimize turbulence as blood enters the branches 35, thereby substantially reducing the likelihood of damage to the blood.

Returning again to FIG. 1, each branch 35 also preferably has an expandable member 55 located proximate the drainage holes 80 for occluding the vena cavae to substantially isolate the vena cavae from the right atrium, and keep the right atrium substantially blood-free. The expandable members 55 are secured to the branches 35 in any conventional manner, and are expanded by expanding means (not shown) providing an inflation medium, such as saline or air, in communication therewith via secondary lumens 85. The expanding means may be an air pump, a fluid pump, syringe, or any other suitable mechanism. Preferably, the expandable members 55 are balloons well known in the art, and are inflated in a manner well-known in the art.

Figure 4:
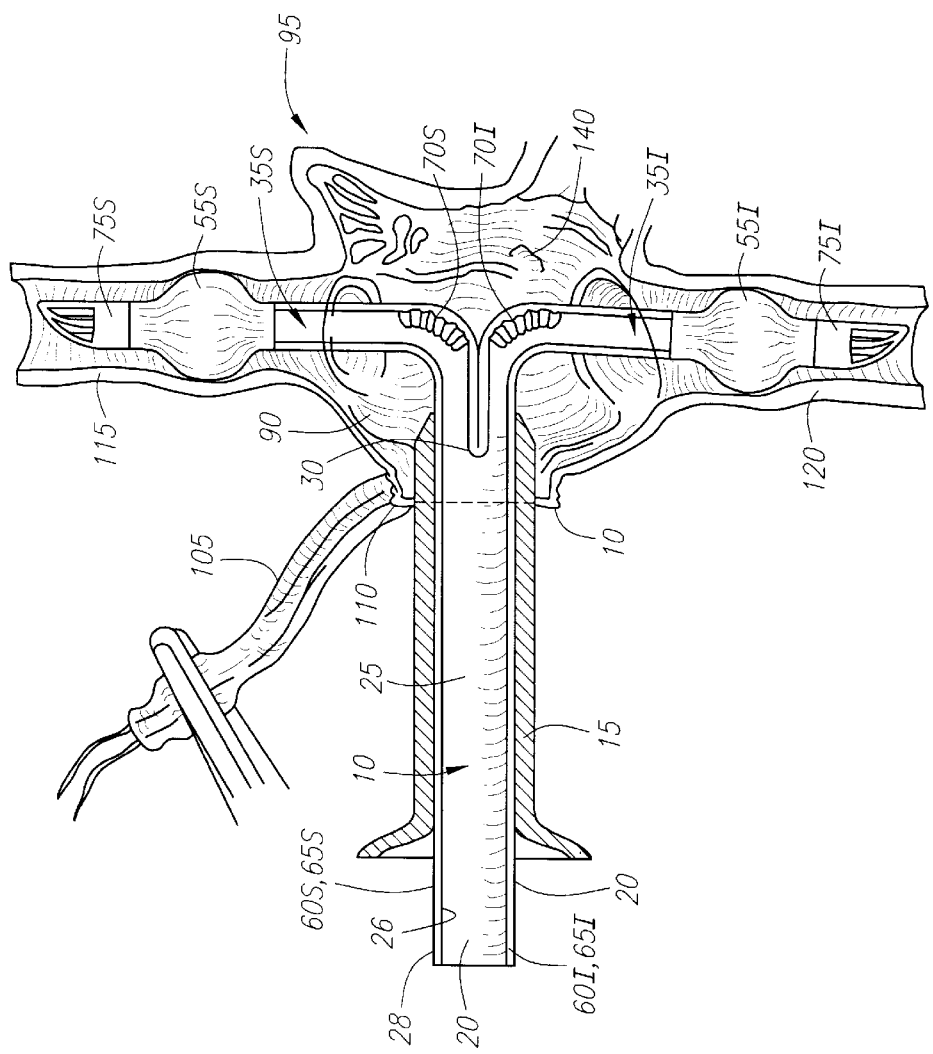
FIG. 4 is a cut-out view of a heart, showing the cannula of FIG. 1 deployed therein.

Turning now to FIG. 4, a cannula 10 according to a preferred embodiment of the present invention is shown entering the right atrium 90 of a heart 95 through a trocar 15 placed therein. The trocar 15 is secured and the incision at the auricle 100 of the right atrium 90 is sealed using conventional techniques. For example, a tourniquet 105 may be used to thread a purse string suture 110. It can be seen in FIG. 4 how branch 35S is directed into or follows the SVC lumen 115, while branch 35I follows the IVC lumen 120. The expandable occluding members 55 are shown occluding the SVC 115 and IVC 120, and the distal tips 75 are positioned to drain or siphon blood through the cannula 10.

Figure 7:
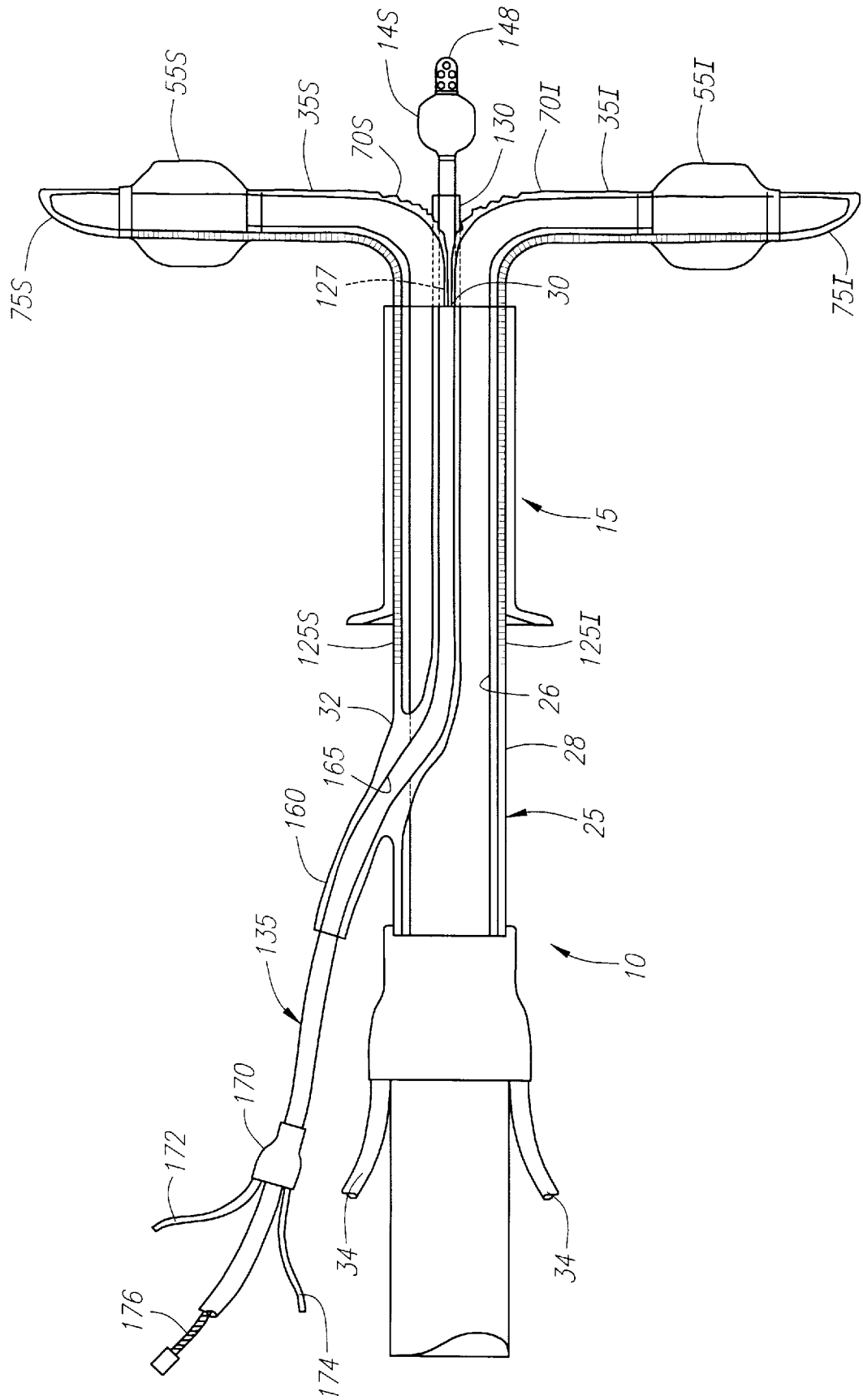
FIG. 7 is a cross section of the cannula of FIG. 5, taken along line 7—7, showing a side port in communication with an axial lumen of the cannula.

An alternate embodiment of the present invention is shown in FIGS. 5 and 7, which show a cannula 10 adapted for use with a cardioplegia delivery device. The flat surfaces 50 of branches 35 in this embodiment have a groove 125, preferably having a semicircular or "C" shaped cross-section formed, e.g., cut or molded, therein. Thus, when the flat surfaces 50 of branches 35 abut each other when the cannula is in a retracted position, the grooves 125 cooperate to form a substantially cylindrical longitudinal secondary lumen 127 (see FIG. 6A) for receiving a cardioplegia delivery cannula 130 which in turn receives a cardioplegia delivery catheter 135. In exchange for the benefit of lumen 127, however, branch lumens 150 will be slightly less voluminous. Alternatively, an imaging device, such as a relatively small diameter, flexible endoscope or an ultrasound imaging device (not shown), may be advanced through the secondary lumen 127, or in a further alternative, a pair of lumens 127A, 127B (see FIG. 6B) may be provided for simultaneous use of the cardioplegia delivery catheter 135 and an imaging device (not shown). In a further alternative, an imaging device may be provided on, e.g., mounted or otherwise attached to, the cardioplegia delivery cannula 130, the cardioplegia delivery catheter 135 or one of the branches 35 adjacent to the elbow portions 72.

A "C" shaped groove as used in this application means not only literally C-shaped, but also includes generally any semi-circular or curved groove that cooperates with an opposing groove that is substantially its mirror image, combining to define a lumen having a recognizable perimeter such as a circle or ellipse.

As shown in FIG. 7, the common primary body 25 preferably includes a side port 160 on a proximal portion 28 thereof, which may be molded or otherwise attached to an outer wall 32 of the common primary body 25, and a pair of inflation lumens 34 communicating with the interior of the occlusion balloons 55. A lumen 165 extends through the side port 160 distally through the common primary body 25, preferably concentric with the outer wall 32 of the common primary body 25. The lumen 165 communicates with the lumen 127 defined by the grooves 125 in the branches 35, thereby providing a continuous lumen from the side port 160 distally beyond the branches 35. Preferably, the side port 160 and lumen 165 intersect the primary lumen 26 of the common primary body 25 with a substantially smooth transition, thereby substantially minimizing the risk of thrombosis forming or otherwise damaging blood flowing through the primary lumen 26, as should be appreciated by those skilled in the art.

The cardioplegia delivery catheter 135 includes a proximal end 170 and a distal portion 138. The proximal end 160 may include an inflation port 172 in communication with the interior of the occlusion balloon 145, and a cardioplegia port 174 in communication with one or more outlets 148 distal to the occlusion balloon 145 on the distal portion 138. In addition, the cardioplegia delivery catheter 135 may include a lumen therein (not shown) to facilitate advancing the catheter 135 over a guidewire 176, as will be appreciated by those skilled in the art.

In use, the cannula 25 may be introduced, along with the trocar 15, into the right atrium 90, similar to the methods described above. During insertion of the cannula 25, it may be desirable to view or otherwise image the procedure by advancing an imaging device through the lumen 165, 127, for example, to view the deployment of the branches 35 within the right atrium 90. Once the cannula 25 is in place, the cardioplegia delivery cannula 130 and/or the cardioplegia delivery catheter 135 may be directed into the side port 160 (after withdrawal of any imaging device therein), and advanced through the lumen 165, 127 into the right atrium 90. The cardioplegia delivery catheter 135 may then be guided into the coronary sinus 140 for retrograde delivery of cardioplegia fluid into the coronary sinus tract 155 as indicated by arrow 160. This may be accomplished by first placing the guidewire 176 in the coronary sinus and/or with the aid of an endoscope or other imaging device (not shown). The occluding balloon 145 may be inflated within the coronary sinus to substantially isolate the coronary sinus from the right atrium, i.e., to prevent substantial leakage of cardioplegia fluid back into the right atrium 90. Thus, with a single device, venous blood drainage and cardioplegia delivery may be accomplished through a single incision, and in a manner that keeps the right atrium substantially blood-free.

While certain embodiments are illustrated in the drawings and have just been described herein, it will be apparent to those skilled in the art that many modifications can be made to the embodiments without departing from the inventive concepts described.

What is claimed is:

1. A cannula for draining blood from the superior and inferior vena cavae of a heart comprising:
   a common primary body having proximal and distal portions, the common primary body having a bifurcation point at the distal portion;
   first and second branches connected to the common primary body and extending distally therefrom, bifurcating from each other at the bifurcation point and terminating at respective first and second distal tips; and
   first and second inflatable members on the first and second branches respectively, the inflatable members being in fluid communication with first and second inflation ports respectively.

2. The cannula as in claim 1, wherein the branches each have a D-shaped transverse cross-section.

3. The cannula as in claim 1, wherein the branches each have pre-shaped stiffening elements for biasing the branches towards predetermined angles with respect to a central longitudinal axis of the cannula.

4. The cannula as in claim 3, wherein the predetermined angle of the first branch is approximately 45°, and the predetermined angle of the second branch is approximately 45°.

5. The cannula as in claim 3, wherein the predetermined angle of the first branch is approximately 90°, and the predetermined angle of the second branch is approximately 90°.

6. The cannula as in claim 3, wherein the branches each have a flat surface, an arced surface, and a D-shaped transverse cross-section, such that when the cannula is in a fully retracted position with the flat surfaces of the branches facing inwardly toward each other and the arced surfaces of the branches facing outwardly away from each other, the branches form a substantially continuous extension of the primary common body of the cannula.

7. The cannula as in claim 3, wherein the branches have accordion-like ridges thereon.

8. The cannula as in claim 1, wherein the branches each have a flat surface and an arced surface, and the flat surfaces each have a groove therein such that when the flat surfaces face each other when the cannula is in a retracted position, the grooves cooperate to form a longitudinal secondary lumen.

9. The cannula as in claim 1, wherein the distal tips of the branches each have drainage holes.

10. The cannula of claim 1, wherein the first and second branches include pre-shaped stiffening elements for biasing the first and second branches away from one another to form an angle of between about 90° and about 180° therebetween.

11. A cannula for draining blood from the superior and inferior vena cavae of a heart comprising:
   a common primary body having proximal and distal portions, the common primary body having a bifurcation point at the distal portion; and
   first and second branches extending distally from the common primary body, bifurcating from each other at the bifurcation point and terminating at respective first and second distal tips;
   the branches each having a flat surface and an arced surface, the flat surfaces each having a groove therein such that when the cannula is in a retracted position with the flat surfaces of the branches abutting each other, the grooves cooperate to form a longitudinal secondary lumen.

12. The cannula as in claim 11, further comprising an imaging device disposed within said longitudinal secondary lumen.

13. A venous drainage cannula for draining blood from the superior and inferior vena cavae of a heart comprising:
   a common primary body having a proximal end and a distal end, and a longitudinal axis;
   first and second branches extending distally from the common primary body, the branches each having a substantially D-shaped transverse cross section such that each branch has an arced surface and a flat surface, the branches being biased towards a tripartite configuration wherein the branches extend substantially transversely with respect to the longitudinal axis, the branches being constrainable in a retracted position wherein the flat surfaces of the branches abut one another and the arced surfaces of the branches face away from each other, such that the branches form a substantially continuous extension of the primary common body, and the transverse cross section of the cannula therefore has a substantially uniform perimeter.

14. The cannula as in claim 13, further comprising a trocar into which the cannula is adapted to be received for constraining the branches in the retracted position.

15. The cannula as in claim 14, further comprising first and second aligners secured on the first and second branches respectively, the aligners biasing the branches towards the tripartite configuration such that when the cannula is inserted into the right atrium of a heart, the distal tip of the first branch is oriented toward the heart's superior vena cava, and the distal tip of the second branch is oriented toward the heart's inferior vena cava, the branches achieving the predetermined orientations when the branches are extended through the trocar sleeve.

16. The cannula as in claim 15, further comprising expandable occluding members on the distal tips of the branches.

17. A method for introducing a bicaval cannula into the right atrium of a patient's heart for draining blood during cardiac surgery, comprising the steps of:
providing a bifurcated cannula having a main body and first and second branches extending distally from the main body,
inserting the branches into the right atrium in a retracted condition wherein the first and second branches abut one another to assume a profile substantially similar in cross-section to the profile of the main body; and
directing the first and second branches away from one another until the branches assume a tripartite configuration, and the first and second branches enter the superior and inferior vena cavae, respectively.

18. The method of claim 17, wherein the branches are biased towards the tripartite configuration, and wherein the branches are constrained in the retracted condition during insertion into the right atrium.

19. The method of claim 18, comprising the additional steps of:
directing the bifurcated cannula into a trocar to constrain the branches in the retracted condition; and
inserting the trocar with the branches in the retracted condition through an incision in the wall of the heart into the right atrium.

20. The method of claim 19, wherein the trocar is withdrawn proximally after insertion into the right atrium while substantially retaining the branches therein, thereby automatically directing the branches away from one another as the branches are deployed from the trocar.

21. The method of claim 18, wherein the branches include pre-shaped stiffening elements for biasing the branches towards the tripartite configuration.

22. The method of claim 21, wherein the pre-shaped stiffening elements are attached to the branches prior to insertion into the right atrium, and wherein the pre-shaped stiffening elements are removed from the branches after the first and second branches are positioned within the superior and inferior vena cavae, respectively.

23. The method of claim 21, wherein the pre-shaped stiffening elements are inserted into supplemental lumens in the branches to attach the pre-shaped stiffening elements to the branches and to bias the branches towards the tripartite configuration.

24. The method of claim 17, comprising the additional step of expanding occlusion members on the first and second branches to substantially isolate the superior and inferior vena cavae, respectively, from the right atrium.

25. The method of claim 17, wherein the branches include surfaces adapted to abut one another when the branches are in the retracted condition, and wherein the branches include grooves extending axially along the surfaces, the grooves together at least partially defining a lumen when the branches are in the retracted condition, the lumen extending proximally into the main body.

26. The method of claim 25, comprising the additional step of advancing an imaging device through the lumen to view the right atrium prior to directing the first and second branches away from one another.

27. The method of claim 17, comprising the additional step of imaging the right atrium with an imaging device advanced through the cannula.

* * * * *